(12) United States Patent
Makdissi

(10) Patent No.: US 8,849,413 B2
(45) Date of Patent: Sep. 30, 2014

(54) LEAD FOR IMPLANTABLE CARDIAC PROSTHESIS WITH INTEGRATED PROTECTION AGAINST THE EFFECTS OF MRI FIELDS

(71) Applicant: Sorin CRM S.A.S., Clamart (FR)

(72) Inventor: Alaa Makdissi, Paris (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/959,423

(22) Filed: Aug. 5, 2013

(65) Prior Publication Data

US 2013/0317562 A1 Nov. 28, 2013

Related U.S. Application Data

(63) Continuation of application No. 13/529,492, filed on Jun. 21, 2012, now Pat. No. 8,521,300.

(30) Foreign Application Priority Data

Jun. 21, 2011 (FR) ...................................... 11 55435

(51) Int. Cl.
*A61N 1/00* (2006.01)
*A61N 1/37* (2006.01)
*A61N 1/05* (2006.01)
*A61N 1/08* (2006.01)
*H03H 1/00* (2006.01)

(52) U.S. Cl.
CPC ................ *A61N 1/3718* (2013.01); *A61N 1/05* (2013.01); *A61N 2001/086* (2013.01); *H03H 1/0007* (2013.01); *A61N 1/056* (2013.01)
USPC ......................................................... 607/62

(58) Field of Classification Search
CPC ....... A61N 1/05; A61N 1/056; A61N 1/3718; A61N 2001/086; A61N 1/3605; A61N 1/36; A61N 1/08; H03H 1/0007
USPC ......................................................... 607/62
See application file for complete search history.

(56) References Cited

U.S. PATENT DOCUMENTS 7,123,013 B2 10/2006 Gray
7,689,288 B2 * 3/2010 Stevenson et al. .............. 607/63
(Continued)

FOREIGN PATENT DOCUMENTS

EP 2 198 917 6/2010

OTHER PUBLICATIONS

Preliminary Search Report for French Patent Application No. 1155435, dated Jan. 27, 2012, 2 pages.

*Primary Examiner* — George Manuel
(74) *Attorney, Agent, or Firm* — Foley & Lardner LLP

(57) ABSTRACT

A lead for an implantable cardiac prosthesis having an integrated protection against the effects of magnetic resonance imaging ("MRI") fields. A protection circuit (26) may be placed at the distal end of the lead comprises a resistive component (28) interposed between the electrode (E1, E2) and the distal end of the conductor (22, 24) associated with this electrode. A normally-open controlled active switch (34, 36) may allow in its closed state to short-circuit the resistive component. A control stage (32) may be coupled to the conductors and detect the voltage of a stimulation pulse applied on the conductor(s), and selectively control by this voltage the closing of the active switch for a duration at least equal to the duration of detected stimulation pulse.

19 Claims, 3 Drawing Sheets

(56) References Cited

U.S. PATENT DOCUMENTS

| | | |
|---|---|---|
| 8,260,412 B2 | 9/2012 | Krause et al. |
| 2003/0204217 A1 | 10/2003 | Greatbatch |
| 2007/0255332 A1 | 11/2007 | Cabelka et al. |
| 2007/0288058 A1 | 12/2007 | Halperin et al. |
| 2008/0154348 A1 | 6/2008 | Atalar et al. |
| 2009/0149909 A1 | 6/2009 | Ameri |
| 2009/0163980 A1 | 6/2009 | Stevenson |
| 2009/0204171 A1 | 8/2009 | Ameri |
| 2010/0076508 A1 | 3/2010 | McDonald et al. |
| 2010/0106227 A1 | 4/2010 | Min et al. |
| 2010/0160989 A1 | 6/2010 | Legay |

* cited by examiner

LEAD FOR IMPLANTABLE CARDIAC PROSTHESIS WITH INTEGRATED PROTECTION AGAINST THE EFFECTS OF MRI FIELDS

CROSS-REFERENCE TO RELATED APPLICATIONS

The present application is a continuation of U.S. application Ser. No. 13/529,492, entitled "Lead for implantable cardiac prosthesis, comprising integrated means of protection against the effects of MRI fields," filed Jun. 21, 2012, which claims the benefit of French patent application Ser. No. 11/55435, entitled "Lead for implantable cardiac prosthesis, comprising integrated means of protection against the effects of MRI fields," filed Jun. 21, 2011, both of which are hereby incorporated by reference in their entireties.

FIELD

The present invention relates to an active implantable medical device as defined by the Jun. 20, 1990 directive 90/395/CEE of the European Community Council, and more specifically to the devices that continuously monitor a patient's cardiac rhythm and deliver if and as necessary to the heart electrical pulses for stimulation, cardiac resynchronization, cardioversion and/or defibrillation in response to a detection of a rhythm disorder.

Active implantable medical devices typically have a housing generally designated as "generator", electrically and mechanically connected to one or more "leads" having electrodes that are intended to come into contact with the myocardium at sites suitable for the detection (collection) of electrical potentials and/or the application of stimulation pulses. These electrodes can be endocardial electrodes (e.g., placed in a cavity of the myocardium in contact with the wall thereof), epicardial electrodes (e.g., in particular to define a reference potential for application of a shock), or intravascular electrodes (e.g., is introduced into the coronary sinus in a location facing the wall of the left ventricle).

The present invention thus more particularly relates to techniques for protecting these devices (e.g., generators and their associated leads) when the patient must be subjected to examination by magnetic resonance, imaging (MRI).

BACKGROUND

An MRI examination is currently contraindicated for patients having an implanted cardiac pacemaker or defibrillator. This is due to the following types of problems that might arise during an MRI examination:

Heating near the electrodes connecting the generator to the patient's heart;
The forces and torques exerted on the device immersed in the high static magnetic field of the MRI machine; and
Unpredictable behavior of the device itself, due to exposure to the extreme magnetic fields.

The present invention is directed to a solution to the first type of problem, namely, the heating problem that appears mainly close to the electrodes, located at the distal end of the leads that are connected to the generator.

Leads placed in an MRI imager act like antennas and collect the radio frequency field (RF) emitted by the imager. The frequency of this RF field is equal to the Larmor frequency of protons, that is $f=42.56 \times B_{01}$ wherein $B_{01}$, in Tesla, is the characteristic static induction of the imager. For typical static induction $B_0$ of 1.5 T or 3 T, the RF frequencies generated by the imager are correspondingly about 64 MHz and 128 MHz, respectively.

Induced currents circulate in the conductors of the leads immersed in the RF field, therefore generating heat which in turn heats the surrounding blood and tissue. In fact, because heating at the electrodes is proportional to the density of current flowing in the latter, the smaller the surface of the electrode, the larger the current density and therefore the higher the heating of surrounding tissues.

In practice, depending on the configuration of the generator, the leads and the MRI imager, the temperature rise experimentally observed typically reaches from 8° C. (for carbon electrodes) to 12° C. (for metal electrodes), and as high as 30° C.

However, the temperature increase should not exceed what is specified in the EN 45502-1 standard and its derivatives, and preferably be less than 2° C. Indeed, a temperature rise of 4° C. causes a local cell death that has for immediate effect, among others, to irreversibly change the detection and stimulation thresholds.

It is certainly possible, as described in U.S. Patent Publication Nos. 2003/0204217 A1 and 2007/0255332 A1, to provide an MRI safety mode in which a protection circuit, provided at the generator connector isolates the circuit conductors of the generator, and connects the conductors to the ground of the generator to prevent circulation of parasitic induced currents. However, this approach is problematic because it prevents the device from remaining functional for the duration of the MRI examination. Because an MRI examination may last several minutes, it is therefore highly desirable that the device can continue seamlessly to detect depolarization potentials and deliver stimulation pulses to the myocardium as needed. This is so even though, during the MRI examination, the device may be switched to a particular secured mode of operation, notably disabling the circuitry sensitive to strong magnetic fields such as the RF telemetry circuits and the switching power supplies.

It is thus not considered to be sufficient in practice to simply disconnect and/or put ground all conductors of the lead during the MRI examination.

Another set of techniques previously proposed to reduce the currents induced by an MRI field are based on placing in series with the lead conductor(s) connected to the electrode (s), i.e., in the path of the induced currents, an impedance opposing the passage of the current during an MRI examination situation. It may be a single series coil (as disclosed in U.S. Pat. No. 7,123,013 B2). However, the mitigation, if it is significant, is not generally sufficient. It was also proposed to insert in the current loop a resonant circuit such as a tank circuit tuned to the RF frequency generated by the MRI imager, as described for example in Patent Publication Nos. 2009/0204171 A1 and 2007/0288058 A1. But this solution has the disadvantage of requiring as many filters as there are different characteristic frequencies of the imager types (e.g., 64 MHz, 128 MHz).

The EP 2198917 A1 and its counterpart US Patent Publication No. 2010/0160989 (both assigned to Sorin CRM S.A.S, previously known as ELA Medical) propose another approach, in the case of a bipolar lead, of disconnecting one of the conductors and connecting it to the ground of the generator housing, so that the grounded conductor can provide shielding protection for the other conductor, which remains functional. This technique is however restricted to bipolar leads; in addition, it requires a modification of the hardware design of the generator, so that the latter can achieve the necessary ground switching on detection of a MRI field.

Other known techniques propose to disable the electrode by a switch disposed in the vicinity thereof and controlled on detection by the generator of an MRI field detected by a sensor incorporated in the latter, as described in US Patent Publication No. 2010/0106227 A1. But the transmission of the command from the generator to the switch located in the lead head, at the other end, requires the presence of an additional conductor, hence the need to design a specific lead and also a specific generator and a specific connector. There is therefore no compatibility with existing leads or generators.

The US Patent Publication No. 2008/0154348 A1 proposes a passive, protection circuit located at the distal end of the lead and not requiring an additional connecting conductor. The principle is to place a PIN diode in parallel with a resistor in series with the electrode. The major drawback of this type of protection is that to compensate for the voltage drop across the diode (about 0.6 to 0.7 V) it is necessary to apply stimulation pulses having a far higher voltage than otherwise necessary. This need is permanent because the protection circuit is purely passive and must remain connected all the time. The loss in the protection diode can be more than half of the stimulation energy, with a major impact on the autonomy and useful lifetime of the device, whose duration may be reduced from 30 to 50%.

The U.S. Patent Publication No. 2009/0149909 A1 describes a comparable system for protection, wherein the lead conductor is provided at its distal end with a series resistor whose terminals are coupled to a "normally closed" switch, controlled by a controller analyzing the voltage at the terminals of this resistor. This device, like the one described above, not only has the disadvantage of creating losses that may affect the autonomy of the device, but also to be sensitive to spurious signals of high amplitude; in fact, any signal whose amplitude exceeds the threshold voltage of the controlled switch causes closure thereof and therefore neutralization of the series resistance of protection, with a corresponding risk of damage to heart tissue.

OBJECT AND SUMMARY

It is therefore an object of the present invention to propose a new lead configuration comprising a protection circuit that can ensure in all circumstances a "self-protection" of the lead against the deleterious effects of MRI fields without involving the generator.

Broadly, the invention is directed to a lead of the type disclosed in US patent Publication No. 2008/0154348 A1 cited above, which is incorporated by reference herein in its entirety, that is to say a lead comprising at its proximal end, a connector to be connected to a generator of an active implantable medical device and, at its distal end, at least one detection/stimulation electrode connected to an associated conductor extending along the lead body to the connector, and a protection circuit that protects against the deleterious effects of an exposure of the lead to magnetic fields likely to be encountered during an MRI examination. The protection circuit is interposed at the distal end of the lead, preferably coupled between the electrode and its associated conductor, and comprises at least one series dipole with a selectively modifiable impedance including a resistive component permanently mounted between the two terminals of the dipole. The dipole further comprises a controlled active switch having a normally open state and a closed state. In the closed state, the controlled active switch provides a short circuit across the resistive component, for example, by coupling the pads of the resistive component or the terminals of the dipole. The lead is also essentially free of a specific conductor for connection of the protection circuit to the generator.

In one embodiment, the active switch in the closed state bypasses the resistive component with a short circuit, and a control stage is provided which comprises a filter used to discriminate between stimulation pulses and phenomena related to MRI induced currents. This discriminator filter, which is preferably interposed between the active switch and a means for applying the voltage of the stimulation pulse, is a low-pass filter whose cutoff frequency is selected to pass the frequency band of a stimulation pulse, e.g., between 1 MHz and 10 MHz, and to block the typically higher frequency band of a signal induced by a MRI imager magnetic field.

In an embodiment having a unipolar lead comprising a single electrode for detection/stimulation connected to a respective single conductor, the control stage can be a circuit coupled between the two terminals of the resistive component of the series dipole with a selectively modified impedance.

In an embodiment having a bipolar lead, comprising two distinct detection/stimulation electrodes connected to two respective conductors, the control stage can be a circuit coupled between the two conductors, near the electrodes at the distal end of the lead.

In one particular embodiment suited to functioning with a monophasic stimulation pulse, the control stage comprises a capacitor charged by the voltage of the stimulation pulse, and a discharge resistor for this capacitor. This capacitor-resistor set has an RC time constant for selectively controlling the closure of the active switch for a time at least equal to the nominal duration of discharge of the capacitor of the output stage of the generator to which the lead is intended to be connected.

In this case, the lead comprises means for charging the capacitor by the voltage of the stimulation pulse with a rectifier dipole advantageously comprising a transistor whose channel conduction is controlled by the output of a comparator whose input terminals are coupled to the two terminals of the rectifier dipole.

In one embodiment with a bipolar lead suited to functioning with a monophasic stimulation pulse, the control stage comprises a minimum-maximum (or absolute value) circuit coupled between the two conductors for delivering a voltage of constant sign (e.g., always positive) for the duration of the stimulation pulse, and a capacitor being charged by the voltage delivered by the minimum-maximum circuit.

In one embodiment with a unipolar lead, comprising a single detection/stimulation electrode connected to a respective single conductor, the control stage advantageously comprises a low-pass filter interposed between the active switch and the means for applying the stimulation pulse voltage. The low-pass filter has a cutoff frequency selected for passing the frequency band of a stimulation pulse, and blocking the frequency band of a signal induced by a MRI magnetic field.

Advantageously, the present invention:
does not require the detection of a MRI field by a sensor of the generator;
does not require any additional conductor in the lead;
is usable with any generator, without hardware changes of the circuits thereof; and
does not contain any constituent such as a diode capable of causing substantial incremental energy consumption during delivery of stimulating pulses to the electrodes.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

With reference, to the drawings FIGS. 1-6, preferred embodiments of a device in accordance with the present invention will now be described. In general, it should be understood by one of ordinary skill in the art that the protective configuration of the present invention can be used not only for protection against MRI fields, but also as protection in various other electromagnetic environments including those created by medical devices such as electrosurgical devices, transcutaneous electrical stimulation of nerves (TENS), and equipment of everyday life such as anti-theft gates, and electrical article surveillance monitors (EAS).

Figure 1:
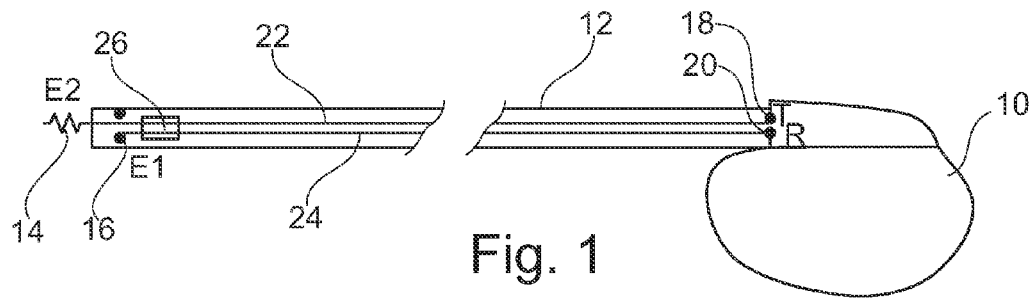
FIG. 1 is a schematic view of a generator and a lead having a protection circuit according to a preferred embodiment of the present invention.

In FIG. 1, an active implantable medical device is schematically shown comprising a generator 10 having its lead 12. In the shown example, lead 12 is a bipolar lead 12 comprising at its distal end a first electrode E2, which is a distal or tip electrode (T) 14 of relatively small area, e.g. an anchoring screw in the cardiac wall. The second electrode E1 is, for example, a ring electrode (R) 16.

The two electrodes E1 and E2 are located at the distal end of the lead 12 and are respectively connected to associated conductors 22, 24, extending along the entire length of the lead body. At their distal end, conductors 22, 24 are connected to the poles 18, 20 of a connector located at the proximal end of the lead, which are in turn connectable to two respective terminals T and R of the generator 10 (See also FIG. 2). The connector combines mechanical and electrical coupling of the proximal end of lead 12 to implantable generator 10.

Figure 2:
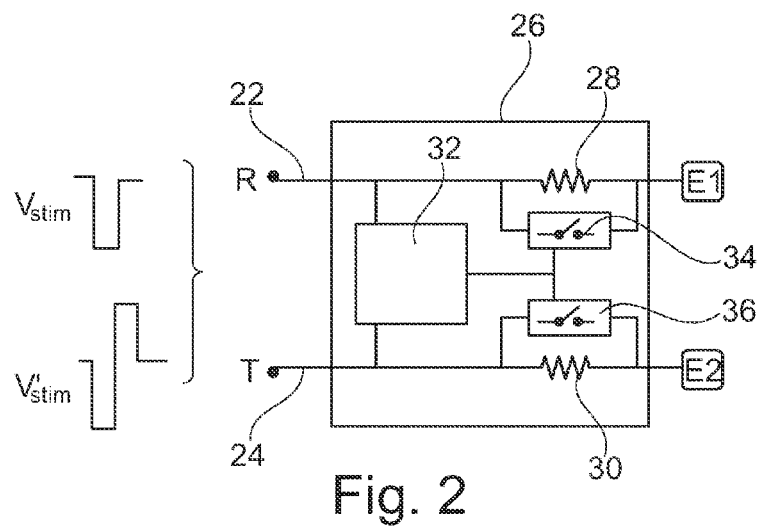
FIG. 2 is a functional block diagram of the protection circuit of FIG. 1.

Lead 12 is provided with a protection circuit 26 disposed at its distal end, close to the two electrodes E1 and E2. With reference to FIG. 2, the elements of one embodiment of protection circuit 26 are shown. In this embodiment, protection circuit 26 is interposed between, on the one hand, electrodes E1 and E2 and, on the other hand, conductors 22 and 24. Protection circuit 26 comprises a resistive component 28, 30, here a resistor 28 interposed between the permanent electrode E1 and its associated conductor 22, and a resistor 30 permanently interposed between the electrode E2 and its associated conductor 24. These resistors 28, 30 have, for example, a value of about 20 kΩ each, sufficient to ensure permanent protection against excessive currents that might be induced in the conductors by an MRI field. This impedance value makes it possible to detect in all circumstances the cardiac potentials by the electrodes E1 or E2 in the presence or absence of an MRI field.

For stimulation, however, it is necessary to disable resistors 28, 30. This function is performed by a control stage 32, which operates to collect and retain the stimulation voltage appearing between conductors 22 and 24 and use this voltage for controlling active switches 34, 36 to close and thereby short-circuit the respective resistors 28, 30, thus allowing the passage of the stimulation current without losses in protection circuit 26.

The controlled active switches 34, 36 are preferably solid state switches, advantageously implemented in MOS technology, more preferably CMOS, with their state "normally open". In terms of current flow, each of resistors 28, 30 is always in series in the current loop of its corresponding electrode, except during periods when the switches 34 and 36 are controlled "closed" by the control stage 32.

With reference to FIG. 2, in the case of a monophasic stimulation pulse such as the illustrated $V_{stim}$ pulse, it is necessary to disable resistors 28, 30 not only during the period of application of the $V_{stim}$ pulse to the diseased tissue, but also for a period sufficient to allow the discharge of the "output capacitor" formed by the interface between cardiac tissues and the stimulation electrode (this discharging period is named Output Capacitor Discharge ("OCD") or charge dumping). The pulse width of $V_{stim}$ is preferably on the order of from 100 µs to 1 ms, and the duration of the OCD phase is preferably on the order of about 20 ms. Control stage 32 must store the stimulation pulse voltage $V_{stim}$ so as to activate and maintain switches 34, 36 closed for the duration of the OCD phase. However, in the case of a biphasic stimulation pulse such as the $V_{stim}$ pulse that is illustrated, the polarity reversal eliminates the need for implementation of an OCD function, because the output capacitor discharge comes from itself due to the polarity reversal of the applied Voltage $V_{stim}$.

The overall impedance of lead 12, as seen from connectors 18, 20 of generator 10, can thus take two different values:

A low value of approximately 20Ω, for the duration of a pacing pulse plus the duration of the OCD phase immediately following, and A high value, typically 20 kΩ, the rest of the time.

Figure 3:
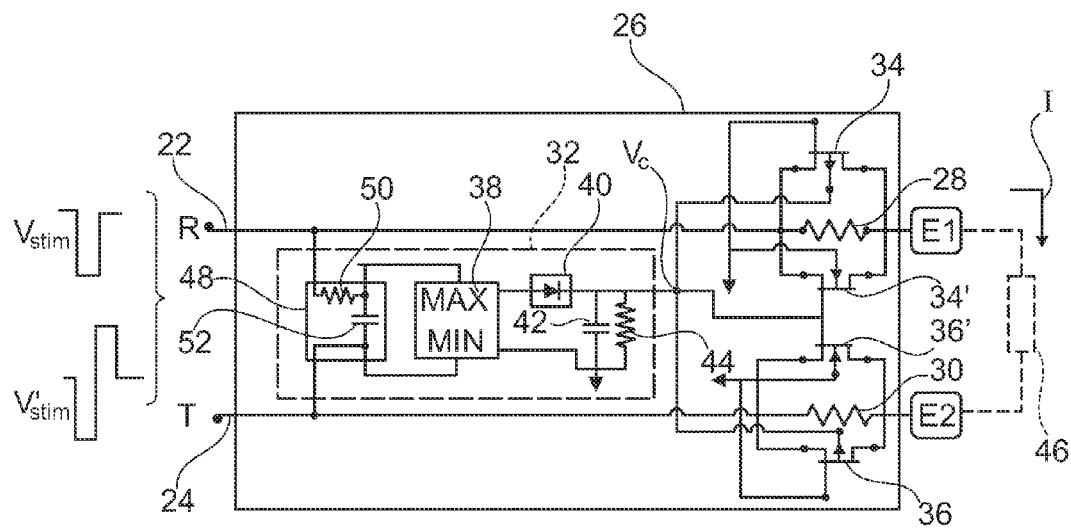
FIG. 3 illustrates a first embodiment of the protection circuit of FIG. 2, for a bipolar lead and monophasic pulse stimulation.

With reference to FIG. 3, an exemplary embodiment of protection circuit 26 is shown adapted to bipolar lead and monophasic pulse stimulation. In this embodiment, resistors 28, 30 are each short-circuited by a pair of complementary CMOS transistors, respectively 34, 34' and 36, 36'. The gates of these transistors are controlled by a control voltage $V_c$ delivered by control stage 32. Control stage 32 includes first a low-pass filter 48, for example, a first order filter comprising a resistor 50 and a capacitor 52. The cutoff frequency of filter 48 is selected so that it passes the frequency band of a stimulation pulse (typically between 1 MHz and 10 MHz) and blocks the frequency band corresponding to a signal induced by an MRI magnetic field. Thus, filter 48 makes it possible to block parasitic MRI signals and pass, the stimulation pulses.

Downstream of low-pass filter 48 is a "minimum-maximum" or "absolute value" ("Min-Max") circuit 38, which is of known construction and outputs an always positive voltage, regardless of the polarity of the stimulation pulse applied to input circuit 26 (and which passes through low-pass filter 48). This output voltage is used to load via a rectifier stage 40, a capacitor 42 across which the control voltage $V_c$ is used to control controlled switches 34, 34' and 36, 36'.

A discharge resistor 44 is mounted across capacitor 42, and its value is selected so that the RC time constant which determines the discharging time of capacitor 42 after the disappearance of the stimulation pulse $V_{stim}$ remains above the control threshold of controlled (MOS) switches 34, 34', 36, 36' for a time sufficient to allow the OCD phase discharge of the output stage of generator 10. In other words, the RC time constant sets, by a simple hardware solution, the time to hold the active switches closed to short-circuit resistors 28, 30.

Thus, control stage 32 discriminates (via filter 48) between undesirable MRI signals and the desired cardiac pacing signals. In the latter case, control stage 32 stores in capacitor 42, via Min-Max circuit 38 and rectifier 40, a very small fraction of the stimulation energy. The V, voltage of capacitor 42 controls the switches for by-passing resistors 28, 30 for a limited time, defined by resistance 44 (discharge time constant of capacitor 42).

Discriminator filter 48 avoids triggering the closing of the switches in the case of a parasitic MRI signal whose amplification would exceed the threshold voltage of the switches 34, 34', 36, 36', by on the order of approximately 1 V.

On the other hand, resistor 44 for discharging capacitor 42 prevents the switches from being closed for a long period after stimulation, which might, during this period, open the passage to any spurious signal to the heart.

Figure 5:
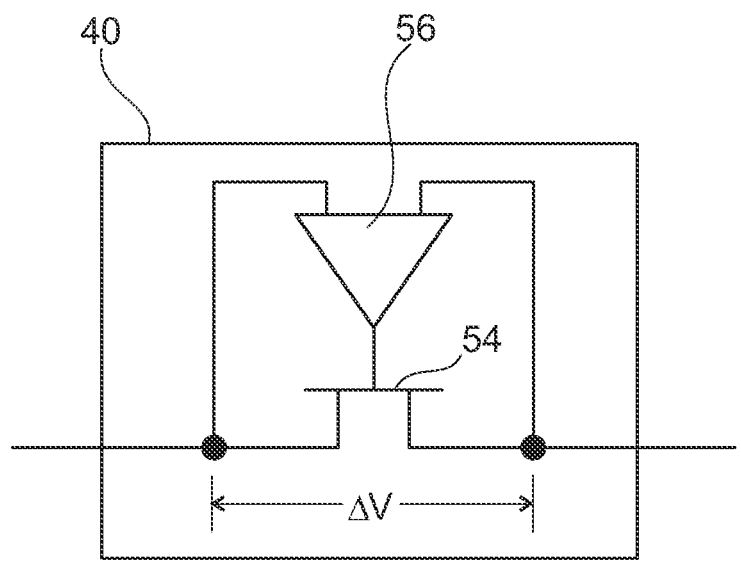
FIG. 5 illustrates a preferred embodiment of the rectifier stage of the control circuit of the switches, to minimize the voltage drop and therefore the electrical losses, at this level.

In one embodiment, the rectifier stage 40 can be achieved simply in the form of a diode. It may also be, more advantageously, implemented as shown in FIG. 5, with an MOS transistor 54 whose channel conduction is controlled by the output of a comparator 56, and whose input terminals are coupled to the two terminals of MOS transistor 54. According to the polarity of the potential across transistor 54, the comparator either outputs or does not output a release signal for transistor 54, thereby either turning it on in one direction or leaving the transistor blocking in the other direction. Compared to a simple diode, this comparator-transistor configuration allows to have across the rectifier pole 40 a very low voltage drop ΔV, around 0.1 V, much lower than the forward voltage drop of a simple diode of about 0.7 V. Electrical losses are reduced accordingly. It must be remembered that this circuit is only powered by the energy stimulation pulses, and it is thus advantageous to reduce energy consumption to optimize the useful lifetime of the implanted device.

Note that, in general, the circuit shown in FIG. 3 may be used either with monophasic pulses $V_{stim}$ (and this, regardless of the polarity of the pulse) or biphasic pulses $V'_{stim}$.

In one embodiment where stimulation is exclusively by monophasic pulses, the polarity thereof is known, as stimulation is always operated in negative polarity. It is not necessary to provide a Min-Max circuit 38 in this embodiment, and capacitor 42 can directly be loaded by the voltage at the output of low pass filter 48.

In an embodiment in which stimulation is exclusively by biphasic pulses, circuit 38 is however necessary to neutralize the effect of polarity reversal, but conversely the function of discharging capacitor 42 (the OCD function permitted by resistance 44) is no longer necessary because the charges accumulated at the heart/electrode interface are canceled due to the polarity reversal of the stimulation pulse applied at this point.

Figure 4:
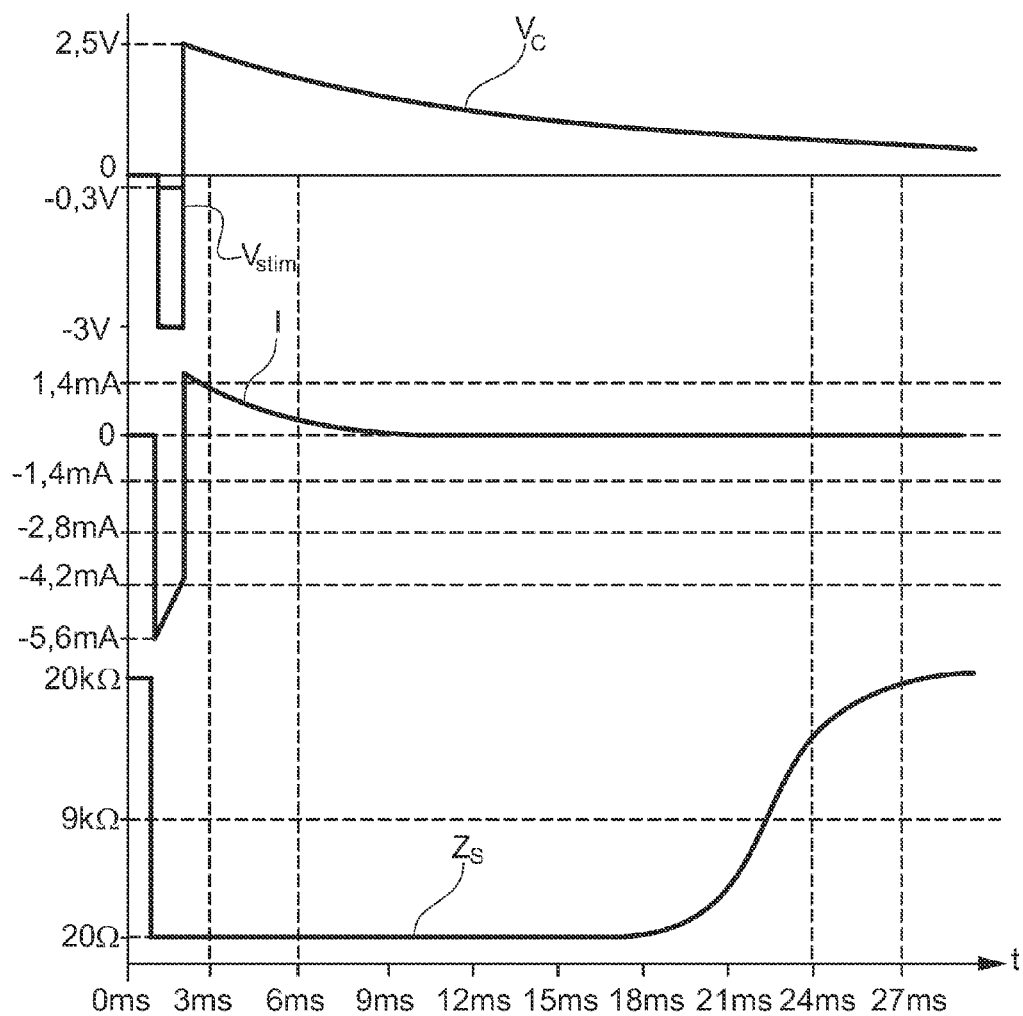
FIG. 4 is a series of timing diagrams showing the variations of different parameters of the protection circuit of FIG. 3 during a representative application of a stimulation pulse.

With reference to FIG. 4, a series of timing diagrams showing the changes in various parameters of the circuit of FIG. 3 during the application of a stimulation pulse are presented. The top timing diagram is the stimulation pulse $V_{stim}$ and the control voltage $V_c$ issued by control stage 32 which gradually decreases due to the RC time constant, on the order of 15 ms, of the capacitor 42-44 resistor set.

The middle timing diagram shows the current I passing in the cardiac tissue, modeled by impedance 46 in FIG. 3 (body impedance), on the order of 500Ω. The timing diagram at the bottom shows the change in the overall impedance $Z_s$ of lead 12, as seen from generator 10:

Normally, that is to say just before application of the stimulation pulse, the impedance is high (e.g., about 20 kΩ) ensuring permanent protection against possible currents, notably induced by an MRI;

At the moment of application of the stimulation pulse $V_{stim}$, this impedance drops almost instantaneously to a low value, on the order of 20Ω, due to the closing of active controlled switches 34, 34', 36 and 36'. This low impedance is maintained for a period of at least on the order of 20 ms, necessary for the OCD discharge after application of the stimulation pulse.

From the hardware implementation viewpoint, it must be noted that the active circuits can be realized in standard CMOS technology, to integrate into a single specific ASIC device all the components of the protective circuit 26 (with the exception of capacitor 42). This circuit can have very small dimensions, typically less than 0.2×0.2 mm, which can be housed in the lead head, near the electrodes.

Another embodiment may be adapted to a bipolar lead and biphasic pulse stimulation. In this case, it is no longer necessary to have an OCD discharge of the output stage of the generator, and the storage of the stimulation voltage beyond the application time of the pulse is no longer necessary. The stimulation voltage $V_{stim}$ can then be applied to the gates of the switches through simple resistors of appropriate value; for example, 10 kΩ. One resistor is connected between a first conductor and the gate of two switches, and another resistor is connected between the other conductor and the gate of the other two switches. The configuration of the protection resistors and of active switches is the same as in the first embodiment shown in FIG. 2. The circuit is only controlled by the stimulation pulse voltage $V_{stim}$; it is sufficient if its amplitude is at least equal to the threshold voltage of the MOS transistors, of the order of 0.7 V, a value compatible with most common pacing configurations.

Figure 6:
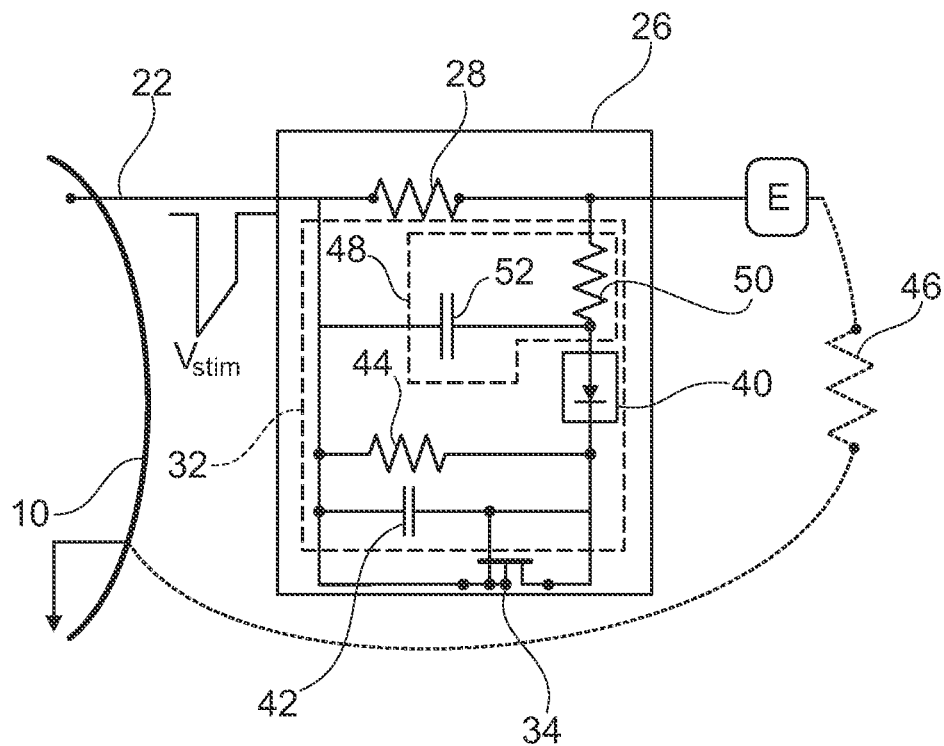
FIG. 6 illustrates an alternate embodiment of a protection circuit in accordance with the present invention, for unipolar lead and monophasic pulse stimulation.

With reference to FIG. 6, another embodiment suitable to a unipolar lead and to monophasic pulse stimulation, is shown. The unipolar lead only comprises (at least functionally) one electrode E, connected by a conductor 22 to one of the terminals of generator 10. The closure of the current loop is carried out by the ground of generator housing 10, as illustrated in FIG. 6. Protection circuit 26 always includes resistor 28 inserted in series between conductor 22 and electrode E, and normally open active switch 34 for selectively short-circuiting resistor 28. It is no longer possible in this case to monitor the voltage fluctuations between two terminals R and T as in the embodiment of FIGS. 2 and 3, because the potential of generator 10 is not directly accessible by circuit 26, which is not connected to it.

The monitoring of the voltage drop is then performed though the serial resistance of resistor 28 of the protection circuit: if the voltage drop across resistor 28, after filtering and rectifying, is greater than the threshold voltage of the transistor 34, then control voltage $V_c$ can be used, as before, to charge a capacitor 42 (associated with a discharge resistor 44). The voltage V, across resistance 42 is used to gate switch 34. Low-pass filter 48 consists, as in the embodiment of FIG. 3, of resistor 50 and capacitor 52. The time constant RC of low-pass filter 52, 50 is selected to be on the order of 10 µs, corresponding to a cut-off frequency of 20 kHz to reliably ensure a discrimination between a stimulation pulse (which essentially only contains low frequency components) and a phenomenon related to an induced MRI current (with mainly high frequency components).

In the first case (pacing pulse), and only in this case, the voltage of the pacing energy is transmitted to capacitor 42 via rectifier stage 40 to charge the capacitor by a small fraction of the stimulation pulse energy. The control voltage $V_c$ across capacitor 42 is transmitted to switch 34, which short-circuits resistor 28 and thus lowers the overall impedance of lead 12 from about 20 kΩ to about 20Ω, as in the previous embodiments. This reduction in impedance is operated for a time sufficient to allow the OCD phase discharge of the output capacitor stage of generator 10, a period determined by the RC time constant of capacitor 42 and its discharge resistor 44.

Again, to minimize energy losses in the protection circuit, rectifier stage 40 may be formed, as illustrated in FIG. 5, in the form of a transistor controlled by a comparator, instead of a simple diode.

One skilled in the art will appreciate that the present invention may be implemented by embodiments other than those described above, which are provided for purposes of explanation and illustration, and not of limitation.

The invention claimed is:

1. A lead for an implantable medical device, comprising:
    at least one electrode;
    at least one conductor;
    a resistive component positioned between the at least one electrode and at least one conductor and configured to protect against a current induced by a magnetic field during an MRI procedure;
    one or more switching components having a first configuration and a second configuration, wherein, in the first configuration, the one or more switching components are configured to provide a short circuit across the resistive component and provide a path for current to flow from the at least one conductor to the at least one electrode around the resistive component, and wherein, in the second configuration, the one or more switching components are configured to open the short circuit, such that the only path for current to flow from the at least one conductor to the at least one electrode is through the resistive component;
    a control circuit configured to control the one or more switching components to place the one or more switching components in the first configuration or the second configuration, wherein the control circuit is configured to detect a stimulation pulse based on a voltage of the stimulation pulse and to place the one or more switching components in the first configuration for a duration of the stimulation pulse;
    a filter circuit configured to at least partially block signals having a first range of frequencies associated with signals induced by the magnetic field during the MRI procedure, wherein the filter circuit is further configured to at least partially pass signals having a second range of frequencies associated with stimulation pulses; and
    a selectively modifiable impedance dipole connected in series between the at least one electrode and the at least one conductor, wherein the selectively modifiable impedance dipole comprises the resistive component.

2. The lead of claim 1, wherein the filter circuit comprises a low pass filter circuit having a cutoff frequency configured to pass a frequency band between 1 MHz and 10 MHz.

3. The lead of claim 1, wherein the one or more switching components are in a normally open state in the second configuration and are in a closed state in the first configuration.

4. The lead of claim 1, wherein the filter circuit is interposed between the at least one conductor and the one or more switching components.

5. The lead of claim 1, wherein the lead is a unipolar lead comprising a single electrode and a single conductor, and wherein the control circuit and the filter circuit are coupled between terminals of the resistive component.

6. The lead of claim 1, wherein the lead is a bipolar lead comprising two distinct electrodes respectively connected to two conductors, and wherein the control circuit and the filter circuit are coupled between the two conductors.

7. The lead of claim 1, wherein the lead is configured for operation with a monophasic stimulation pulse, wherein the control circuit comprises a capacitor-resistor set comprising a capacitor configured to be charged by the stimulation pulse and a resistor configured to discharge the capacitor, wherein the capacitor-resistor set has a time constant configured such that the capacitor-resistor set causes the one or more switching components to be placed in the first configuration for the duration of the stimulation pulse during which a capacitor of an output stage of a generator to which the lead is connected is discharged.

8. The lead of claim 7, further comprising a charging circuit configured to charge the capacitor of the capacitor-resistor set using the stimulation pulse, wherein the charging circuit comprises a rectifier dipole having two terminals and a transistor having a conduction channel controlled by an output of a comparator, wherein input terminals of the comparator are coupled to the two terminals of the rectifier dipole.

9. The lead of claim 1, wherein the lead is configured for operation with a biphasic stimulation pulse, and wherein the control circuit is configured to transmit the stimulation pulse to a control terminal of the one or more switching components.

10. An implantable medical device, comprising:
    a generator configured to generate a stimulation pulse; and
    a lead comprising:
    at least one electrode;
    at least one conductor configured to be connected to the generator;
    a resistive component positioned between the at least one electrode and at least one conductor and configured to protect against a current induced by a magnetic field during an MRI procedure;
    one or more switching components having a first configuration and a second configuration, wherein, in the first configuration, the one or more switching components are configured to provide a short circuit across the resistive component and provide a path for current to flow from the at least one conductor to the at least one electrode around the resistive component, and wherein, in the second configuration, the one or more switching components are configured to open the short circuit, such that the only path for current to flow from the at least one conductor to the at least one electrode is through the resistive component;
    a control circuit configured to control the one or more switching components to place the one or more switching components in the first configuration or the second configuration, wherein the control circuit is configured to detect the stimulation pulse from the generator based on a voltage of the stimulation pulse and to place the one or more switching components in the first configuration for a duration of the stimulation pulse; and
    a filter circuit configured to at least partially block signals having a first range of frequencies associated with signals induced by the magnetic field during the MRI procedure, wherein the filter circuit is further configured to at least partially pass signals having a second range of frequencies associated with stimulation pulses, wherein the lead is a bipolar lead comprising two distinct electrodes respectively connected to two conductors, and wherein the control circuit and the filter circuit are coupled between the two conductors.

11. The lead of claim 10, wherein the filter circuit comprises a low pass filter circuit having a cutoff frequency configured to pass a frequency band between 1 MHz and 10 MHz.

12. The lead of claim 10, further comprising a selectively modifiable impedance dipole connected in series between the at least one electrode and the at least one conductor, wherein the selectively modifiable impedance dipole comprises the resistive component.

13. The lead of claim 10, wherein the one or more switching components are in a normally open state in the second configuration and are in a closed state in the first configuration.

14. The lead of claim 10, wherein the filter circuit is interposed between the at least one conductor and the one or more switching components.

15. The lead of claim 10, wherein the lead is a unipolar lead comprising a single electrode and a single conductor, and wherein the control circuit and the filter circuit are coupled between terminals of the resistive component.

16. The lead of claim 10, wherein the lead is configured for operation with a monophasic stimulation pulse, wherein the control circuit comprises a capacitor-resistor set comprising a capacitor configured to be charged by the stimulation pulse and a resistor configured to discharge the capacitor, wherein the capacitor-resistor set has a time constant configured such that the capacitor-resistor set causes the one or more switching components to be placed in the first configuration for the duration of the stimulation pulse during which a capacitor of an output stage of the generator is discharged.

17. The lead of claim 16, further comprising a charging circuit configured to charge the capacitor of the capacitor-resistor set using the stimulation pulse, wherein the charging circuit comprises a rectifier dipole having two terminals and a transistor having a conduction channel controlled by an output of a comparator, wherein input terminals of the comparator are coupled to the two terminals of the rectifier dipole.

18. The lead of claim 10, wherein the lead is configured for operation with a biphasic stimulation pulse, and wherein the control circuit is configured to transmit the stimulation pulse to a control terminal of the one or more switching components.

19. A method for use with an implantable medical device, the implantable medical device comprising a lead comprising at least one electrode, at least one conductor, and a resistive component positioned between the at least one electrode and at least one conductor and configured to protect against a current induced by a magnetic field during an MRI procedure, the method comprising:
blocking, using a filter circuit, at least a portion of signals having a first range of frequencies associated with signals induced in the at least one conductor by the magnetic field during the MRI procedure;
passing, using the filter circuit, at least a portion of signals having a second range of frequencies associated with a stimulation pulse generated by a generator;
placing, using a control circuit, one or more switching components in a first configuration in response to detecting the stimulation pulse based on a voltage of the stimulation pulse, wherein, in the first configuration, the one or more switching components are configured to provide a short circuit across the resistive component and provide a path for current to flow from the at least one conductor to the at least one electrode around the resistive component; and
placing, using the control circuit, the one or more switching components in a second configuration during one or more time periods during which a stimulation pulse is not detected, wherein, in the second configuration, the one or more switching components are configured to open the short circuit, such that the only path for current to flow from the at least one conductor to the at least one electrode is through the resistive component,
wherein the lead further comprises a selectively modifiable impedance dipole connected in series between the at least one electrode and the at least one conductor, wherein the selectively modifiable impedance dipole comprises the resistive component.

* * * * *